United States Patent [19]
Zimmermann et al.

[11] Patent Number: 5,376,119
[45] Date of Patent: Dec. 27, 1994

[54] ATTACHMENT FOR AN ARTIFICIAL LIGAMENT, AND A PROCESS FOR IMPLANTATION

[75] Inventors: Martin Zimmermann, Gwatt/Thun; Joel Tendon, La Neuveville, both of Switzerland

[73] Assignee: Protek AG, Muensingen-Bern, Switzerland

[21] Appl. No.: 146,339

[22] Filed: Nov. 1, 1993

[30] Foreign Application Priority Data

Nov. 2, 1992 [EP] European Pat. Off. ......... 92810839.8

[51] Int. Cl.$^5$ ............................................. A61F 2/08
[52] U.S. Cl. .................................................... 673/13
[58] Field of Search .................. 623/11, 13, 16, 18; 606/72, 73, 60, 88

[56] References Cited

FOREIGN PATENT DOCUMENTS 0238223 9/1987 European Pat. Off. .
0330328 8/1989 European Pat. Off. .

*Primary Examiner*—David Isabella
*Attorney, Agent, or Firm*—Townsend and Townsend Khourie and Crew

[57] ABSTRACT

An attachment for securing an artificial ligament to a bone includes a retaining element supported in a bone (2) for an end section of the ligament (1), which is disposed in a guide duct (3) formed in the bone (2), and a clamping element which can be tightened against the end section. The retaining element is a pin (5) which can be inserted transversely to the pulling direction (Z) of the ligament (1) in a bore hole (8) formed in the bone (2) that intersects the guide duct (3). A through-hole (12) in the pin extends in the direction (Z) and is aligned with the guide duct. The guide duct (3) extends in the pulling direction (Z) of the ligament (1) and the longitudinal axis of the pin is at an enclosed angle (W) of less than 90° relative to direction (Z). The pin (5) contains a through-hole (12) which is oriented transversely to the longitudinal axis (B) of the pin and suitable for the ligament (1) to pass through. An axial bore hole (7) opens into the through-hole and threadably receives the clamping element so that it can be forced against the ligament (1) in through-hole (12). This enables an initial stressing and attachment of the ligament (1) in simple operational steps.

13 Claims, 1 Drawing Sheet

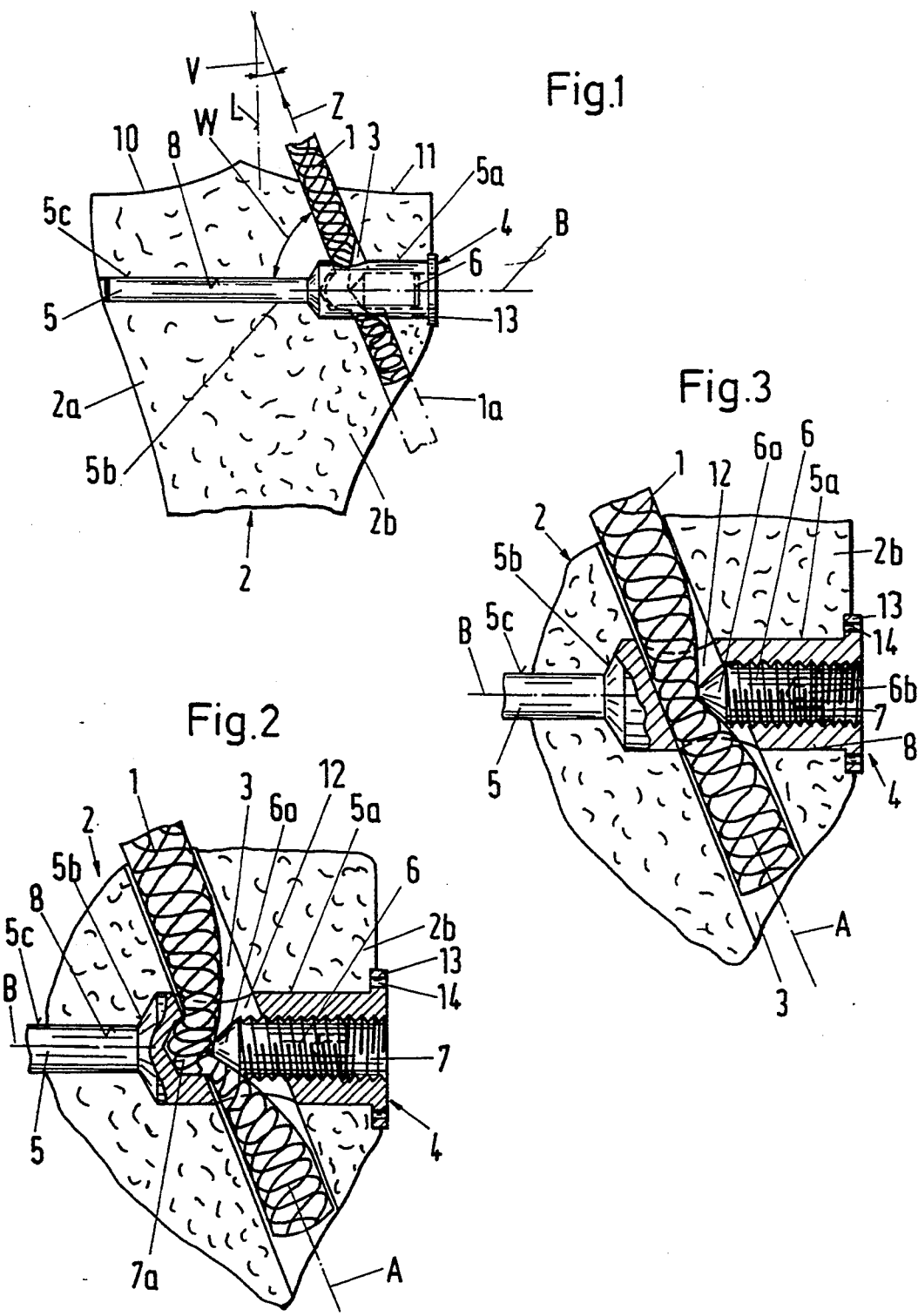

ATTACHMENT FOR AN ARTIFICIAL LIGAMENT, AND A PROCESS FOR IMPLANTATION

BACKGROUND OF THE INVENTION

The invention relates to an attachment for an artificial ligament, in particular a cruciate ligament in a knee joint, which is passed through a guide duct constructed in a bone, the attachment containing a retaining element supported in the bone and receiving an end section of the ligament and a clamping element which can be braced against this end section.

The invention also relates to a process for the implantation of an artificial ligament in a bone by means of such an attachment.

An attachment of the said type known from EP-A-0 465 408 contains a conical attachment sleeve as a retaining element which can be inserted into the guide duct and a radially deformable collet which can be inserted in a self-locking manner therein for retaining the ligament. A similar attachment of the said type is known from EP-A-0 232 049, which shows conical clamping elements which are inserted into a stocking-like ligament extension and are braced via said elements against an attachment sleeve which can be inserted into the guide duct and which sleeve in turn can be subsequently tightened. The known attachments require additional devices and/or relatively expensive adjustment work to tighten or if required to subsequently tighten the implanted ligament in order to coordinate the opposed movements of ligament extension and clamping so that the ligament is established with the desired initial stress.

SUMMARY OF THE INVENTION

The object of the invention is to create an attachment which has been improved in particular in this respect, and which guarantees a precise adjustment and/or resetting of a predetermined initial stress of the implanted ligament with simple means and with low expenditure of labor and time.

The attachment designed according to the invention permits a functional separation of the operational steps required for the regulation of the initial stress of the ligament and for the regulation of the clamping force, by it being possible to adjust the clamping force independently of the respective initial stress of the ligament. By the arrangement specified by the invention, simple premachining is also performed in the bone by it being possible to match the guide duct intended to receive the ligament and the bore hole intersecting it and intended to receive the pin exclusively to the dimensions of the respective part—the ligament or the pin respectively—and to construct them without further subsequent machining. With the design specified by the invention, the ligament can be simply inserted through the guide duct and the through-hole of the pin into the bone and be kept under initial stress on the outside of the bone, e.g. with a spring balance, while the clamping of the ligament occurs independently therefrom by the clamping element, which is guided through the axial bore hole for the pin towards the section of the ligament penetrating the through-hole and is braced by this against a supporting surface of the pin. The ligament can be withdrawn from an endless supply in the appropriate length and after clamping can be cut flush with the outer surface of the bone. The parts of the attachment can also be designed so that they are approximately flush with the bone surface.

The process according to the invention enables the attachment to be mounted gently with respect to the osseous tissue and a secure initial stress and attachment of the implanted ligament in operational steps which are simple to perform and are separate from one another.

BRIEF DESCRIPTION OF THE DRAWINGS

FIG. 1 shows a part of a bone provided with an attachment constructed according to the invention in a longitudinal section;

FIG. 2 shows the attachment according to FIG. 1 in a larger sectional representation; and FIG. 3 shows a corresponding attachment according to a modified embodiment of the invention.

DESCRIPTION OF THE PREFERRED EMBODIMENTS

As shown in FIG. 1, one end of an artificial ligament 1, in the exemplified embodiment shown an artificial cruciate ligament of a knee joint, is guided through a guide duct 3 constructed in a bone 2, in the representation the shin bone (tibia), and held in an attachment 4. The other end of the ligament 1 is held in a counterpart to the bone 1 (not shown), in the present exemplified embodiment the thigh bone (femur), which can be provided with a corresponding attachment 4.

The guide duct 3 is formed by a bore hole, which penetrates the bone 2 at an acute angle V to its longitudinal axis L. The attachment 4 contains a retaining element in the form of a pin 5, which can be inserted transversely to the pulling direction (arrow Z) of the ligament 1, and a clamping element in the form of a locking screw 6, which is disposed in an axial bore hole 7 of the pin 5 and which, as shown, can be designed with a pointed end 6a and also with a hexagon socket 6b. The pin 5 is disposed in a stepped bore hole 8 passing through the bone 2, which bore hole intersects the guide duct 3 and which, together with the section of the guide duct 3 extending in the pulling direction (arrow Z) of the ligament 1 towards the interior of the bone, encloses an angle W of less than 90°. Accordingly a component, determined by the angle W and acting in the axial direction, of the tensile force introduced via the ligament is exerted on the pin 5, by which the pin 5 can be braced via a collar part 13 constructed thereon in FIG. 1 to the left towards the interior of the bone 2. In the example shown the bore hole 8 extends roughly parallel to the "tibia plateau" determined by condyles 10 and 11 of the bone 2, angle W being approximately 60° to 70°. It is obvious that each arbitrary angle W can be chosen to guarantee a component of the tensile force regarded as being adequate.

The locking screw 6 is disposed in an end section 5a of the pin 5, which passes via a tapered neck part 5b into a remaining longitudinal section 5c having a smaller diameter. The end section 5a is designed with a through-hole 12, which penetrates it in the transverse direction and is suitable for the ligament to pass through, and which in the exemplified embodiment shown is formed by a bore hole which can be positioned to align with the guide duct 3, and the diameter of which corresponds with that of the guide duct 3 and the axis A of which together with the longitudinal axis B of the pin 5 encloses an angle which corresponds to the angle W between the guide duct 3 and the bore hole 8 of the bone 2. Instead of the tapered bore hole shown, a corresponding through-slit in the transverse direction may also be provided as a through-hole 12. Into the through-hole 12 opens the axial bore hole 7 of the pin 5 provided with an internal thread, in which the locking screw 6 can be adjusted—in the exemplified embodiment shown with a spanner—and is retained by being braced against the section of the ligament 1 penetrating the through-hole 12. According to the representation shown in FIGS. 1 and 2, the axial bore hole 7 can be designed with a depth which exceeds the corresponding dimension of the through-hole 12, so that the ligament 1 penetrates into the end section 7a of the bore hole 7 when the locking screw 6 is tightened and so that the ligament attachment has additional security.

As shown in the representation according to FIG. 3, the axial bore hole 7 of the pin 5 may also end in the through-hole 12, so that the ligament 1 is pressed against the wall of the through-hole 12 by the locking screw 6—or a corresponding other clamping element—and can be held more gently without additional deformation.

The pin 5 may preferably be designed as a component traversing via the respective cross-sectional dimension of the bone 2, which extends over the two edge parts 2a and 2b of the cortex of the bone 2 which are opposite one another in cross section and is supported with both its ends in these relatively hard edge parts 2a and 2b of the osseous tissue. Accordingly a loading of the relatively soft inner part, the spongiosa, of the osseous tissue by the pin 5 is avoided and a permanent, precise positioning of the pin is guaranteed.

As can be seen from the drawings, the collar part 13 can be formed by a flange-like neck provided on the end section 5a, via which the pin 5 is supported on the outside of the bone 2. The collar part 13 can be substantially flush with the outside of the bone 2 or protrude over it, as shown, by a small amount, e.g. 1 mm. According to the representation, the collar part 13 may also be provided with holes 14 for receiving driving spigots of a positioning instrument (not shown), by which the pin 5 can be inserted, adjusted and removed.

For implanting the ligament 1 in the bone 2, in a first step, for example, a first bore hole corresponding to a predetermined position of the guide duct 3 can be made in the osseous tissue. After this in a second step, e.g. by means of a hole gauge of a known type (not shown), a second bore hole 8 intersecting the first bore hole and intended to receive the longitudinal section 5c of pin 5 is made in the bone with a predetermined angle W, which bore hole is widened in the intersection region according to the dimensions of the end section 5a of the pin 5 to be received. In a third step the pin 5 provided with the through-hole 12 is introduced into the bore hole 8 and positioned with the through-hole 12 aligning with the guide duct 3, the neck part 5b being able to be positioned at a corresponding shoulder part of the bore hole 8. In a fourth step the artificial ligament 1 is passed through the passage formed by the guide duct 3 and the through-hole 12, in which case the lower end of the ligament 1a shown by dot-dash lines in FIG. 1 can be detected outside the guide duct and if necessary can be brought, by means of a spring balance, to a predetermined initial stress if the other end of the ligament is already attached to the counter-piece of the joint (not shown). Finally in a fifth step the locking screw 6 is introduced into the bore hole 7 of the pin 5 and tightened via the section of the ligament 1 penetrating the through-hole 12 against a support part of the pin 5 close to the ligament 1, after which the ligament end 1a protruding from the guide conduit 3 is cut off flush to the outer surface of the bone 2.

It is obvious that the bore hole 8 intended to receive the pin 5 can also be designed as the first bore hole and the guide duct 3 as the second bore hole. Instead of the locking screw shown, any other screw types or an appropriate clamping element, e.g. resilient in use, can be used. The attachment specified by the invention is also suitable for other applications, e.g. in the region of the vertebral column or of the shoulder joint.

What is claimed is:

1. In an attachment for an artificial ligament extending through a guide duct formed in a bone, the attachment including a retaining element supported in the bone receiving an end section of the ligament subjected to a pulling force acting in a pulling direction and a clamping element which can be secured against this end section, the improvement comprising a pin forming the retaining element and disposed transversely to the pulling direction in a bore hole formed in the bone which intersects the guide duct and which also extends in the pulling direction and encloses an angle of less than 90° relative to the pin, the pin including a through-hole oriented transversely to a longitudinal axis of the pin and suitable for the ligament to pass through, and an axial bore opening into said through-hole in which the clamping element is adjustably retained transversely to the section of the ligament in the through-hole.

2. An attachment according to claim 1, wherein, in cross section of the bone, the pin extends over two edge parts of the bone which are opposite one another.

3. An attachment according to claim 1, wherein the through-hole of the pin is a formed hole having a diameter which corresponds to a diameter of the guide duct and an axis which, together with a longitudinal axis of the pin, encloses an angle corresponding to the angle between the guide duct and the bore hole in the bone.

4. An attachment according to claim 1, wherein the through-hole and the axial bore are located at an end section of the pin having a larger diameter than a remaining longitudinal section of the pin.

5. An attachment according to claim 4, wherein the end section and the remaining longitudinal section of the pin are connected to one another via a tapered neck part adapted to be positioned on a shoulder part defined by the bore hole.

6. An attachment according to claim 1, wherein the pin includes a collar part adapted to be positioned on and protruding from an outside of the bone.

7. An attachment according to claim 1, wherein the axial bore hole is a threaded hole, and the clamping element comprises a locking screw threaded into the threaded hole.

8. An attachment according to claim 1, wherein the axial bore hole of the pin has a depth so that it extends beyond the through-hole.

9. A method for attaching an artificial ligament to a bone comprising the steps of:
   providing an elongated ligament retaining pin including a through-hole oriented transversely to a longitudinal axis of the pin and suitable for passing the ligament therethrough, an axial bore extending axially from one end of the pin and opening into the through-hole, and a clamping element adjustably retained in the axial bore of the pin and adapted to extend into the through-bore;

forming a guide duct in the bone for receiving an end section of the artificial ligament;

forming a hole in the bone adapted to receive the pin, the bone hole intersecting the guide duct at a predetermined angle;

introducing the pin into the bone hole and aligning the through-hole of the pin with the guide duct;

extending the artificial ligament through the guide duct in the bone and the through-bore in the pin; and firmly securing the end section of the artificial ligament to the pin and thereby to the bone by forcing the clamping element against a portion of the ligament disposed in the through-hole of the pin to thereby clamp the portion of the ligament between the clamping element and a section of the pin on a side of the through-bore opposite from the clamping element.

10. A process according to claim 9 wherein the predetermined angle is less than 90°.

11. A process according to claim 9 wherein the step of forcing comprises the steps of forming a threaded connection between the pin and the clamping element, and turning the clamping element relative to the pin to thereby advance the clamping element towards and force it against the portion of the ligament and the section of the pin.

12. A process according to claim 11 including the step of inserting the clamping element in the axial bore of the pin after the pin has been placed in the bone hole.

13. A process according to claim 9 wherein the section of the pin includes a depression located on the side of the through-hole opposite from the through-bore, and wherein the step of forcing includes the step of deflecting the portion of the ligament into the depression and out of alignment with the guide duct.

* * * * *